United States Patent
Ryan et al.

(10) Patent No.: US 12,048,596 B2
(45) Date of Patent: Jul. 30, 2024

(54) ERGONOMIC CHANDELIER ENDO-ILLUMINATION PROBE

(71) Applicant: Alcon Inc., Fribourg (CH)

(72) Inventors: Timothy C. Ryan, Laguna Hills, CA (US); Qing Xiang, Irvine, CA (US); Randall T. Ige, Aliso Viejo, CA (US); Robert Jeffrey Heng, Costa Mesa, CA (US)

(73) Assignee: Alcon Inc., Fribourg (CH)

( * ) Notice: Subject to any disclaimer, the term of this patent is extended or adjusted under 35 U.S.C. 154(b) by 213 days.

(21) Appl. No.: 17/475,780

(22) Filed: Sep. 15, 2021

(65) Prior Publication Data

US 2022/0087772 A1   Mar. 24, 2022

Related U.S. Application Data (60) Provisional application No. 63/082,521, filed on Sep. 24, 2020.

(51) Int. Cl.
| | |
|---|---|
| *A61B 90/35* | (2016.01) |
| *A61F 9/007* | (2006.01) |
| *F21V 8/00* | (2006.01) |
| *A61B 90/30* | (2016.01) |

(52) U.S. Cl.
CPC .............. *A61B 90/35* (2016.02); *A61F 9/007* (2013.01); *G02B 6/0008* (2013.01); *A61B 2090/306* (2016.02)

(58) Field of Classification Search
CPC ............ A61B 2090/306; A61B 3/0008; G02B 6/0008; A61F 9/007
See application file for complete search history.

(56) References Cited

U.S. PATENT DOCUMENTS

| | | | | |
|---|---|---|---|---|
| 4,768,858 A | * | 9/1988 | Hussein | A61B 1/00165 |
| | | | | 606/7 |
| 7,731,710 B2 | | 6/2010 | Smith | |
| 8,480,279 B2 | | 7/2013 | Papac et al. | |
| 8,900,220 B2 | * | 12/2014 | Vijfvinkel | A61B 5/0084 |
| | | | | 606/2 |

(Continued)

FOREIGN PATENT DOCUMENTS

EP   3185803 B1   6/2020

OTHER PUBLICATIONS

Alcon Surgical Retina Product Catalog, 2019 (36 pages).

*Primary Examiner* — William J Carter (57) ABSTRACT

Embodiments disclosed herein provide devices, systems, and methods for illuminating inside an eye globe. More particularly, the present disclosure relates to ergonomic chandelier illumination systems for illumination of a surgical site during ophthalmic surgery, the chandelier illumination systems having improved flexibility, profile, and light coupling efficiency. In certain embodiments, a malleable chandelier illumination probe, which is bendable by a surgeon to any desired angle, is disclosed. In certain other embodiments, a preformed chandelier illumination probe, which is preset to a desired angle using a heating method, is disclosed. In certain other embodiments, a method for belling and binding two optical fibers to create a dual chandelier output with improved light coupling efficiency, which is capable of being used with a single connector, is disclosed.

9 Claims, 11 Drawing Sheets

(56) References Cited

U.S. PATENT DOCUMENTS

| | | |
|---|---|---|
| 10,022,200 B2 | 7/2018 | Richmond |
| 10,470,651 B2 | 11/2019 | Vijfvinkel |
| 10,859,748 B2 * | 12/2020 | Mirsepassi .......... G02B 6/0008 |
| 10,888,219 B2 | 1/2021 | Smith et al. |
| 2003/0036756 A1 | 2/2003 | Dubnack et al. |
| 2006/0069386 A1 | 3/2006 | Dubnack et al. |
| 2006/0184162 A1 | 8/2006 | Smith |
| 2008/0177257 A1 * | 7/2008 | Smith ................. G02B 6/0008 |
| | | 606/15 |
| 2015/0018629 A1 | 1/2015 | Vijfvinkel |
| 2016/0066777 A1 * | 3/2016 | Peterson ................ A61F 9/007 |
| | | 600/249 |
| 2019/0011646 A1 | 1/2019 | Jochinsen |
| 2020/0022773 A1 | 1/2020 | Grueebler |
| 2021/0373240 A1 | 12/2021 | Kulkarni |

\* cited by examiner

ERGONOMIC CHANDELIER ENDO-ILLUMINATION PROBE

PRIORITY CLAIM

This application claims the benefit of priority of U.S. Provisional Patent Application Ser. No. 63/082,521 titled "ERGONOMIC CHANDELIER ENDO-ILLUMINATOR PROBE," filed on Sep. 24, 2020, whose inventors are Timothy C. Ryan, Qing Xiang, Randall T. Ige and Robert Jeffrey Heng, which is hereby incorporated by reference in its entirety as though fully and completely set forth herein.

TECHNICAL FIELD

The present disclosure relates to devices, systems, and methods for illuminating an area of the eye. More particularly, the present disclosure relates to ergonomic chandelier illumination systems for illumination of a surgical site during ophthalmic surgery, the chandelier illumination systems having improved flexibility, profile, and light coupling efficiency, and being stable when inserted into a patient's eye.

BACKGROUND

Chandelier illumination systems are useful to provide stationary, wide-angle, and uniform endo-illumination of a surgical site during eye procedures, such as the retina during vitreoretinal surgery. Generally, chandelier illumination systems may be placed through a patient's eye wall (including the sclera) during a bimanual ophthalmic surgery and left disposed therethrough so that the surgeon may use both hands to operate throughout the procedure.

BRIEF SUMMARY

The present disclosure relates to devices, systems, and methods for illuminating inside an eye globe. More particularly, the present disclosure relates to ergonomic chandelier illumination systems for illumination of a surgical site during ophthalmic surgery, the chandelier illumination systems having improved flexibility, profile, and light coupling efficiency, and being stable when inserted into the patient's eye.

In certain embodiments, a malleable chandelier illumination probe is disclosed. The malleable chandelier illumination probe includes a metal wire, an optical fiber, and a sleeve. The metal wire and the optical fiber are housed within the sleeve. The metal wire, the optical fiber, and the sleeve are bound at a binding. An exposed distal portion of the optical fiber extends out of the sleeve. The metal wire is made of a malleable material configured for being bent to an angle before or during a surgical procedure.

In certain other embodiments, a preformed chandelier illumination probe is disclosed. The chandelier illumination probe includes an optical fiber made of a plastic material. The optical fiber has a proximal portion and a distal portion. A portion of the optical fiber between the proximal portion and the distal portion is bent to a predetermined angle between about 70° (degrees) and about 160° prior to a surgical procedure.

In yet certain other embodiments, a method is disclosed. The method includes belling a proximal end of each of a plurality of optical fibers, each of the plurality of optical fibers having the proximal end and a distal end, and combining the belled proximal ends of the plurality of optical fibers in a connector configured to be coupled to a surgical console.

The following description and the related drawings set forth in detail certain illustrative features of one or more embodiments.

BRIEF DESCRIPTION OF THE DRAWINGS

The appended figures depict certain aspects of one or more disclosed embodiments and are therefore not to be considered as limiting the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Embodiments disclosed herein provide devices, systems, and methods for illuminating inside of an eye globe. More particularly, the present disclosure relates to ergonomic chandelier illumination systems for illumination of a surgical site during ophthalmic surgery, the chandelier illumination systems having improved flexibility, profile, and light coupling efficiency. In certain embodiments, a malleable chandelier illumination probe, which is bendable by a surgeon to many (e.g., any) desired angles, is disclosed. In certain other embodiments, a preformed chandelier illumination probe, which is preset to a desired angle using a heating method, is disclosed. In yet certain other embodiments, a method for belling and binding two optical fibers to create a dual chandelier output with improved light coupling efficiency, which is capable of being used with a single connector, is disclosed.

As used herein, the term "proximal" refers to a location with respect to a device or portion of the device that, during normal use, is closest to the console that the des ice is coupled to and farthest from the patient in connection with whom the device is used. Conversely, the term "distal" refers to a location with respect to the device or portion of the device that, during normal use, is farthest from the console and closest to the patient in connection with whom the device is used.

As used herein, the terms "low profile" or "improved profile" refer to the device being lower, slimmer, or more compact than is usual for devices of its type such that, as an example, the risk of interference with other objects near the device is reduced.

Figures 1, 2:
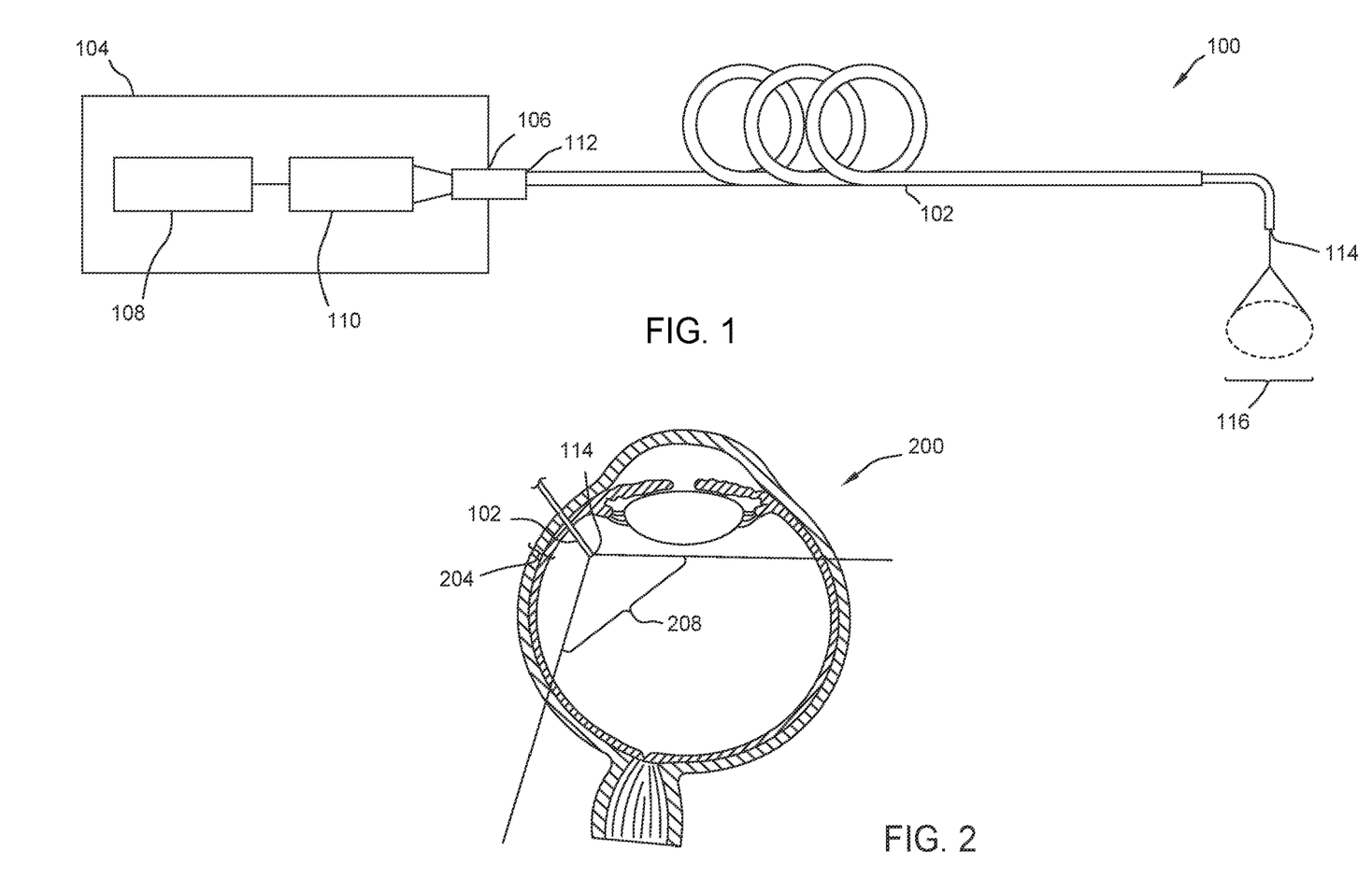
FIG. 1 illustrates a chandelier illumination system, in accordance with certain embodiments of the present disclosure.
FIG. 2 illustrates a cross-sectional view of an eye having a portion of a chandelier illumination probe disposed through the wall of the eye, in accordance with certain embodiments of the present disclosure.

FIG. 1 illustrates a chandelier illumination system 100. The chandelier illumination system 100 includes a chandelier illumination probe 102 coupled to a console 104, such as a surgical console list ophthalmic surgery, including but not limited to, consoles sold by Alcon of Fort Worth, Texas. The chandelier illumination probe 102 includes one or more optical fibers. In certain embodiments, the chandelier illumination probe 102 also includes a sleeve and a metal wire. The proximal end 112 of the chandelier illumination probe 102 is coupled to the console 104 using a connector 106.

The console 104 provides a light source, which in the example of FIG. 1, includes a light engine 108 and an optical condensing element 110. In operation, the light engine 108 emits a light beam that is then condensed and focused by the optical condensing element 110 on an opening at the proximal end of connector 106, where the opening exposes the proximal ends of one or more optical fibers inside the chandelier illumination probe 102. The chandelier illumination probe 102 is operable to transmit the light beam received from the light source such that light is projected from the distal end 114 thereof to illuminate an area 116, such as a portion of the inner eye during ophthalmic surgery.

For example, FIG. 2 illustrates a cross-sectional view of an eye 200 having a portion of a chandelier illumination probe 102 disposed through the wall 204 thereof to provide a source of light in the internal portion of the eye globe. The distal end 114 of the chandelier illumination probe 102 illuminates an internal area of the eye 200 with a light beam having an exemplary width 208.

Figure 3A:
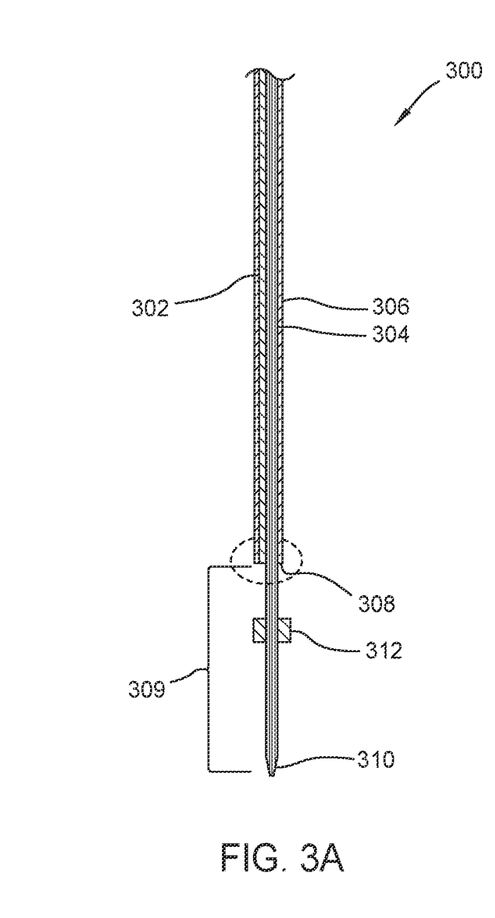
FIGS. 3A-3B illustrate a cross-sectional view of chandelier illumination probe in a straight and bent position, respectively, in accordance with certain embodiments of the present disclosure.
Figure 3B:
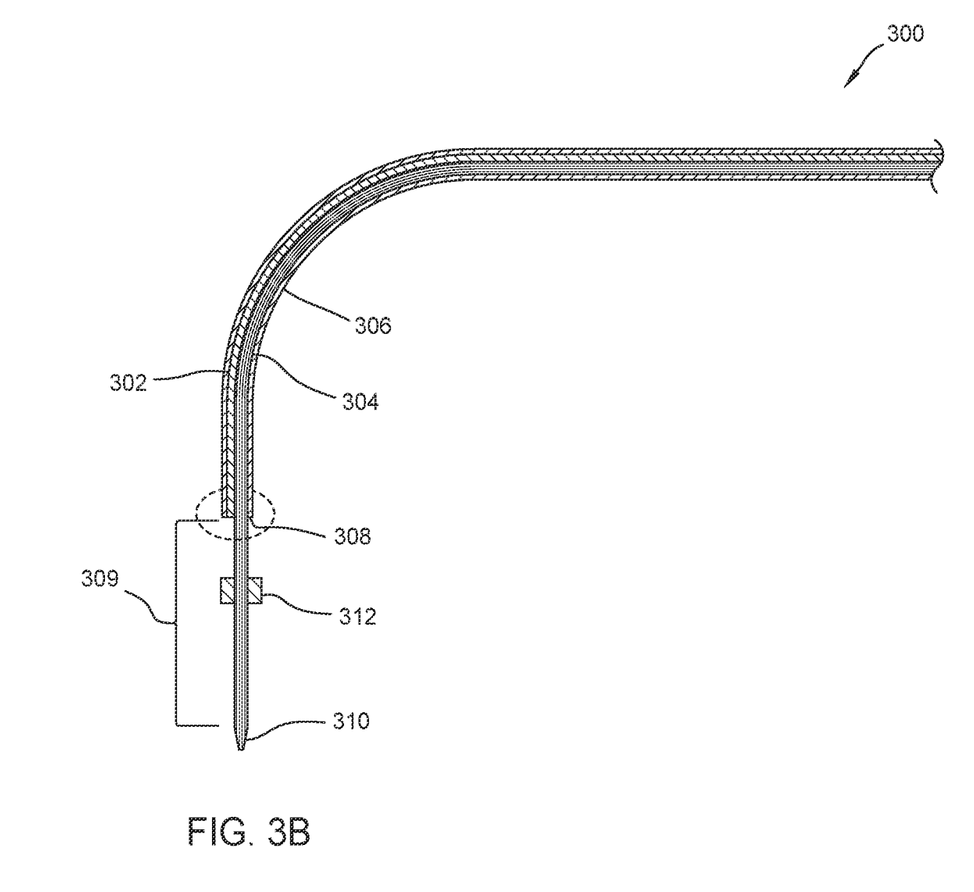
Figures 4A, 4B:
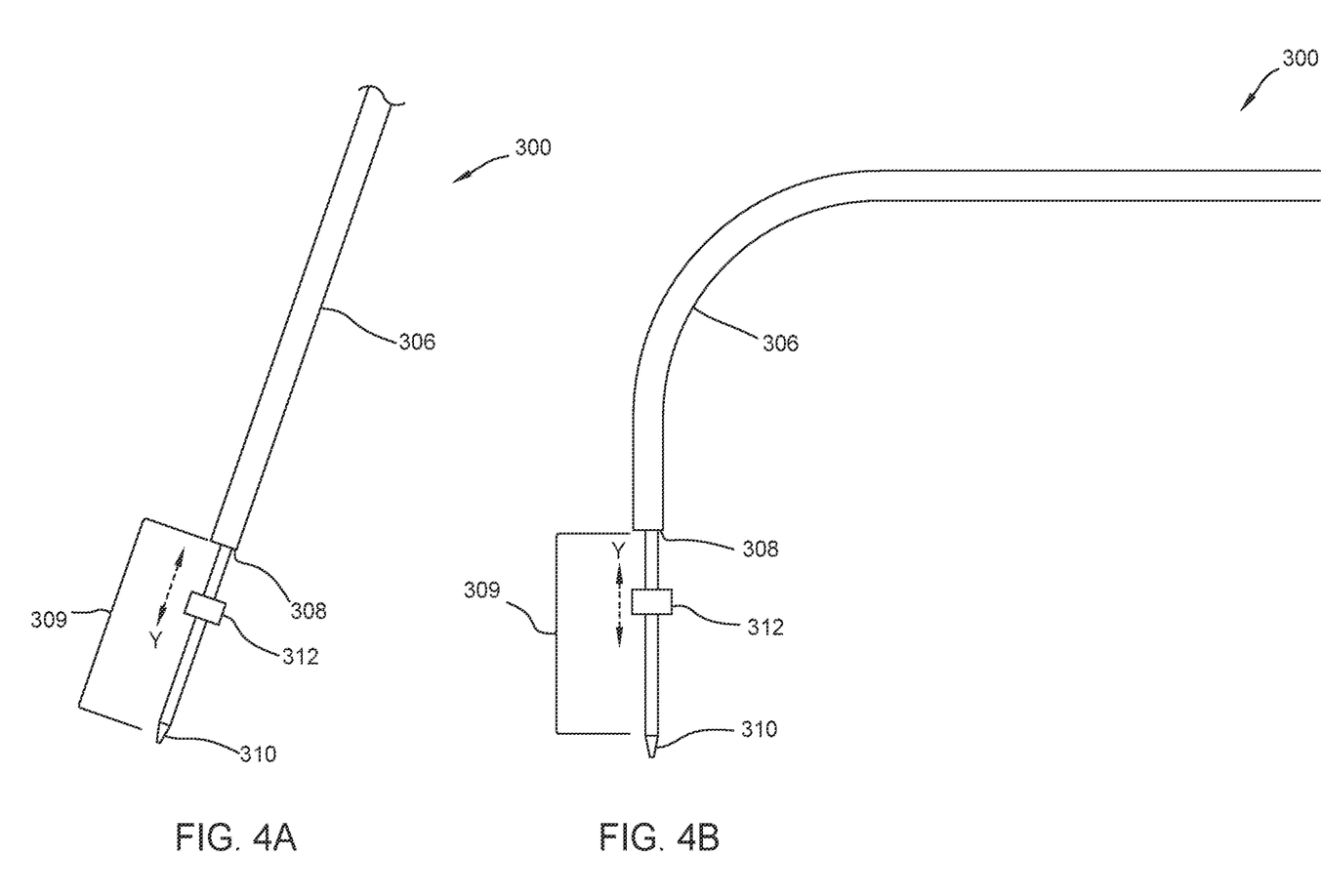
FIGS. 4A-4B illustrate schematic views of the chandelier illumination probe of FIGS. 3A-3B, in accordance with certain embodiments of the present disclosure.

FIGS. 3A-3B illustrate a cross-sectional view of a malleable chandelier illumination probe 300 in a straight and bent position, respectively. FIGS. 4A-4B illustrate schematic perspective views of the malleable chandelier illumination probe 300. In the embodiments of FIGS. 3A-4B, the malleable chandelier illumination probe 300 includes a metal wire 302 and tin optical liber 304, which are housed in a sleeve 306. In some embodiments, the metal wire 302 and the optical fiber 304 are bonded together inside the sleeve 306, for example, using adhesives.

The material and size of each of the metal wire 302, optical fiber 304, and sleeve 306 are selected such as to make the malleable chandelier illumination probe 300 low profile, low mass, and flexible, and simultaneously sturdy enough to retain shape and position while inserted into a patient's eye. As such, a surgeon can bend the malleable chandelier illumination probe 300 to many (e.g., any) desired angles or shapes before or during a surgical procedure such that it will not interfere with other equipment near the surgical site and will retain its position and shape within and outside the user's eye during the surgical procedure, leaving both of the surgeon's hands free to perform the remainder of the surgical procedure. In certain embodiments, the metal wire 302 includes malleable material while the optical fiber 304 and sleeve 306 are made from any suitable flexible materials. In such embodiments, since the metal wire 302 is malleable, when the surgeon bends the metal wire 302, the metal wire 302 takes on the desired angle. Generally, optical fibers, such as optical fiber 304 have inherent shape memory. Since the flexible optical fiber 304 and the sleeve 306 are bound to the malleable metal wire 302, according to certain embodiments of the present disclosure, the optical fiber 304 and the sleeve 306 also advantageously take on the desired angle and/or shape. The desired angle and/or shape are determined by the surgeon based on various considerations, including but not limited to, the presence and position of other equipment and instruments during the ophthalmic surgery, as well as the anatomical structure of the patient's face and eye.

As described above, the metal wire 302 is made of any suitable malleable material. One example of suitable malleable material is stainless steel. In certain embodiments, a diameter of the metal wire 302 is between about 0.1 millimeter (mm) and about 0.5 mm, such as between about 8 thousandths of an inch (Thou) and about 15 Thou (or between about 0.2 mm and about 0.4 mm), for example about 0.3 mm.

In certain embodiments, the sleeve 306 is made of any suitable flexible, thin-walled material. Examples of suitable flexible materials include, but are not limited to, Polyvinyl chloride (PVC)/Pebax, polyethylene, and silicon. In certain embodiments, the sleeve 306 has a diameter between about 0.5 mm and 1.5 mm, such as about 1.00 mm. In certain embodiments, a durometer of the sleeve 306 is between about 30 durometer hardness (D) and about 40 D, such as about 35 D. In certain embodiments, a wall thickness of the sleeve 306 is between about 8 Thou and about 10 Thou, or between about 0.05 mm and about 0.1 mm, such as about 0.08 mm. In certain embodiments, the thickness of the metal wire 302 is generally between about 8 Thou and about 15 Thou (or between about 0.2 mm and about 0.4 mm). In certain embodiments, this selection of material and size of the metal wire 302 and the sleeve 306 provides a chandelier illumination probe 300 that is easily formable and sturdy enough to maintain a formed fiber shape. In certain embodiments, in addition to or instead of using a malleable wire 302, the sleeve 306 itself is made of malleable material. In certain other embodiments, the malleable wire 302 and the sleeve 306 may be coextruded or braided such that the sleeve 306 becomes malleable. In certain embodiments, when a malleable sleeve 306 is used, a malleable wire 302 may no longer be included in the malleable chandelier illumination probe 300. In certain other embodiments, both the wire 302 and the sleeve 306 are malleable. The optical fiber 304 includes any suitable flexible material (e.g., Poly(methyl methacrylate) (PMMA or acrylic)) useful for providing illumination, for example, inside the globe of a patient's eye during ophthalmic surgery. In certain embodiments, the optical fiber 304 is between about 300 microns and about 500 microns, such as about 400 microns.

In certain embodiments, this selection of material and size of the metal wire 302 and the sleeve 306 provides a chandelier illumination probe 300 that is easily formable and sturdy enough to maintain any formed shape. Additionally, in certain embodiments, the material and size of the metal wire 302 and the sleeve 306 reduce the overall mass of the chandelier illumination probe 300 as compared to conventional chandelier illumination probes by eliminating the need for a hub at the termination thereof.

The metal wire 302, optical fiber 304, and sleeve 306 are bound together at the binding 308, such as with the use of adhesives. As shown in FIG. 3, the binding 308 is at the distal end of the sleeve 306 in certain embodiments. An exposed portion 309 of the optical fiber 304 extends beyond the binding 308 from the sleeve 306. The exposed portion 309 terminates at the distal end 310 of the optical fiber 304, from which light is projected to illuminate an area during operation.

The chandelier illumination probe 300 also includes a moveable stopper 312, which is a small slideable disk, useful to prevent the chandelier illumination probe 300 from being advanced too far into or through the patient's eye. The moveable stopper 312 is moveable in a vertical direction (y) along the length of the exposed portion 309 of the optical fiber 304 between the binding 308 and the distal end 310. In certain embodiments, the moveable stopper 312 is vertically moveable when force is applied to overcome the friction between the moveable stopper 312 and the optical fiber 304 along which it is disposed. In certain examples, a surgeon moves the moveable stopper 312 by hand or with a tool, such as forceps, to a desired position along the exposed portion 309. Friction exists between the moveable stopper 312 and the optical fiber 304 because of the material of the moveable stopper 312. The distance between the moveable stopper 312 and the tip of the distal end 310 of the optical fiber 304, which is variable, is selected based on various considerations, such as the desired placement for illumination or the diameter of the patient's eye. When a distal side of the moveable stopper 312 contacts the patient's eye wall or a cannula hub of a cannula assembly, while the chandelier illumination probe 300 is being inserted in the eye, the chandelier illumination probe 300 is stopped from advancing further because of the friction between the moveable stopper 312 and the optical fiber 304. The moveable stopper 312 therefore allows the chandelier illumination probe 300 to be configured for variable insertion depth. In certain embodiments, it is contemplated that the stopper 312 is fixed.

Figure 5:
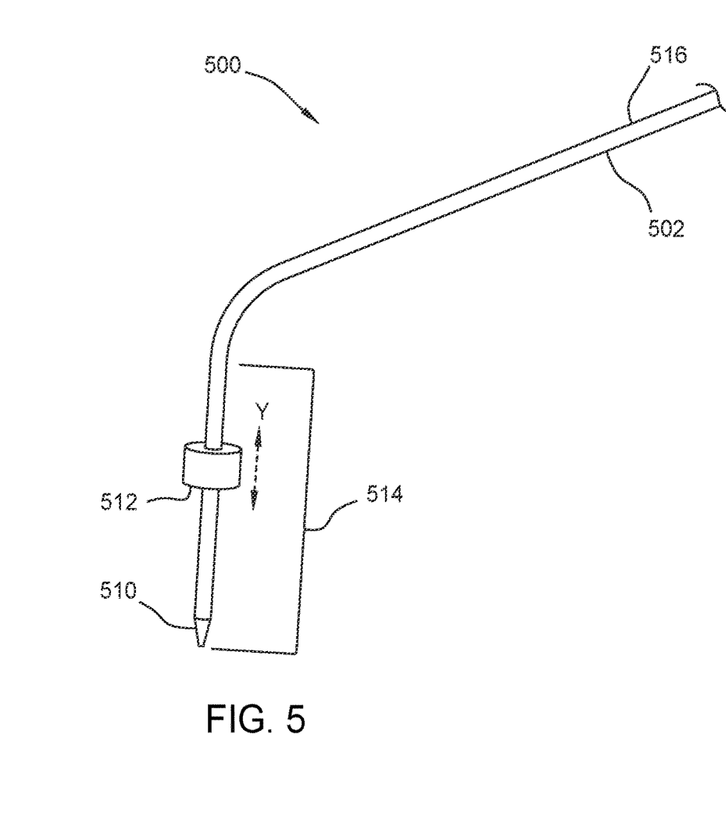
FIG. 5 illustrates a chandelier illumination probe, in accordance with certain embodiments of the present disclosure.

FIG. 5 illustrates a preformed chandelier illumination probe 500, which is bent to a predetermined angle along the length thereof. The preformed chandelier illumination probe 500 includes an optical fiber 502 having a proximal portion 516 and a distal portion 514. The optical fiber 502 is any suitable optical fiber useful for providing illumination, for example, inside the globe of a patient's eye during ophthalmic surgery, which is bendable during a heating method (i.e., thermal bending), such as plastic optical fibers. More particularly, in certain embodiments, the optical fiber 502 of the chandelier illumination probe 500 is selected such that when it is locally heated at a portion thereof, the portion can be bent to a predefined angle between about 70° (degrees) and about 160°. The heating temperature applied should be sufficient to make the optical fiber 502 pliable. In certain embodiments, the heating temperature is between about 200° F. and about 450° F. and the heating occurs for between about 5 seconds and about 20 seconds (other heating temperatures and times are also contemplated us needed to make the optical fiber pliable). The heating temperature and time are related such that the higher the heating temperature, the shorter time used for healing, and the lower the heating temperature, the longer time used for heating. In certain embodiments, the optical fiber 502 is a Poly(methyl methacrylate) (PMMA or acrylic) optical fiber. As shown, the optical fiber 502 is bent at or near the distal portion 514.

Once the local heating method is performed to set the bend of the chandelier illumination probe 500 at the desired angle, the straight memory of the optical fiber 502 is removed and the chandelier illumination probe 500 retains its bent shape. In certain embodiments, the angle of the preformed chandelier illumination probe 500 is not changeable unless another heating method is performed to reshape the angle.

Like the malleable chandelier illumination probe 300, the preformed chandelier illumination probe 500 includes a moveable stopper 512, which is a small slideable disk, useful to prevent the chandelier illumination probe 500 from being advanced too far into or through the patient's eye. The moveable stopper 512 is moveable in a vertical direction (y) along the distal portion 514 of the optical fiber 504. More particularly, the mineable stopper 512 is vertically moveable when force is applied to overcome the friction between the moveable stopper 512 and the optical fiber 502 along which it is disposed. In certain examples, a surgeon moves the moveable stopper 512 by hand or with a tool, such as forceps, to a desired position along the distal portion 514. The distance between the moveable stopper 512 and the tip of the distal end 510 of the optical fiber 504, which is variable, may be selected based on various considerations, such as the desired placement for illumination or the diameter of the patient's eye. When a distal side of the moveable stopper 512 contacts the patient's eye wall or the cannula hub of a cannula assembly, while the chandelier illumination probe 500 is being inserted therethrough, the chandelier illumination probe 500 is stopped from advancing further because of the friction between the moveable stopper 512 and the optical fiber 504. The moveable stopper 512 therefore allows the chandelier illumination probe 500 to be configured for variable insertion depth. In certain embodiments, it is contemplated that the stopper is fixed.

Figure 6:
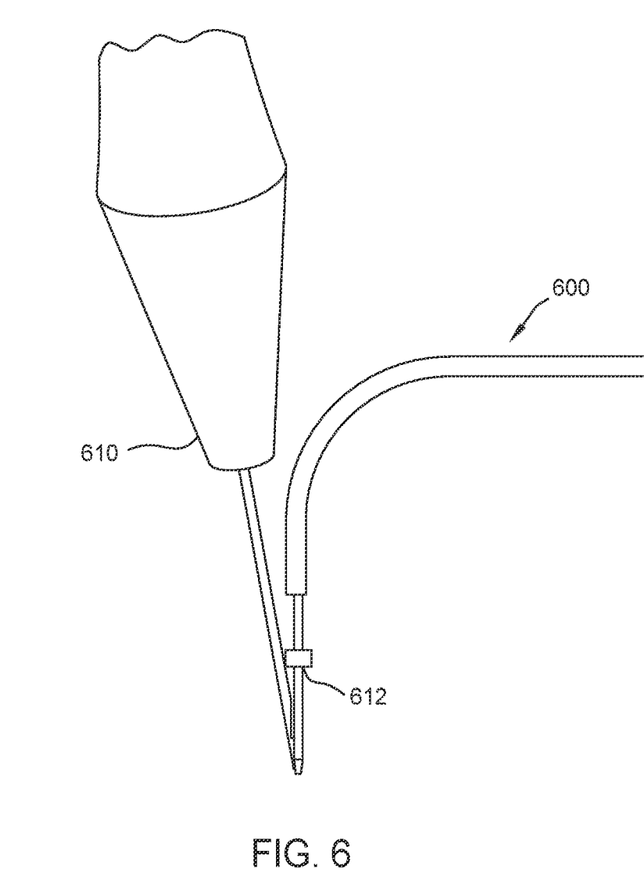
FIG. 6 illustrates a chandelier illumination probe and a guiding needle, in accordance with certain embodiments of the present disclosure.

During an operation, such as ophthalmic surgery, a chandelier illumination probe, such as the chandelier illumination probe 300 or chandelier illumination probe 500, is inserted through the patient's eye wall. The disclosed chandelier illumination probes are advantageously insertable using various cannulated and/or non-cannulated methods. In certain embodiments, as shown in FIG. 6, the chandelier illumination probe 600, such as chandelier illumination probe 300 or chandelier illumination probe 500, is inserted through the patient's eye wall using a guiding needle 610. In certain embodiment, the guiding needle 610 is a separate instrument, which is not attached to the chandelier illumination probe 600. In certain embodiments, the guiding needle 610 and the chandelier illumination probe 600 are coupled as a single piece such that the guiding needle 610 and the chandelier illumination probe 600 are inserted into the patient's eye together, and the guiding needle 610 is then pulled out, but the chandelier illumination probe 600 remains disposed in the patient's eye. The guiding needle 610 pierces an incision through the patient s eye wall, through which the chandelier illumination probe 600 may be inserted, and then guides the chandelier illumination probe 600 through the incision and into the patient's globe. This use of a guiding needle, such as guiding needle 610, is an example of a non-cannulated entry method. Instead of or in addition to using the guiding needle 610, in certain other embodiments, a sharpened distal tip of the chandelier illumination probe 600 may be used to pierce the patient's eye wall before the remainder of the chandelier illumination probe 600 is inserted therethrough.

Alternatively, the disclosed chandelier illumination probes, such as chandelier illumination probes 300 and 500, are inserted through the patient's eye wall using a cannulated entry method. In such methods, a cannula is first inserted through the patient's eye wall and then the chandelier illumination probe is inserted through the cannula.

Figure 7A:
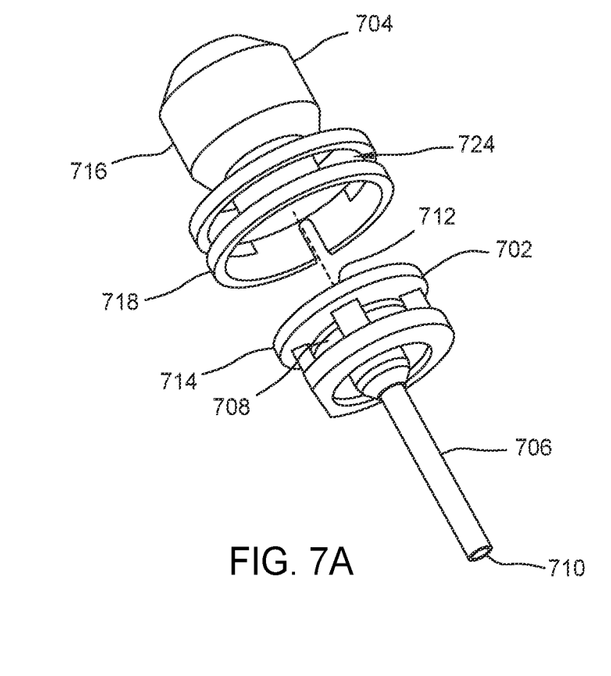
FIGS. 7A-7D illustrate a cannula assembly and an external retention member, in accordance with certain embodiments of the present disclosure.
Figure 7B:
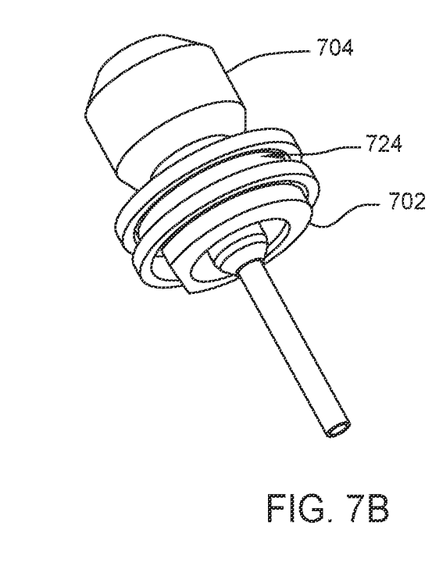
Figure 7C:
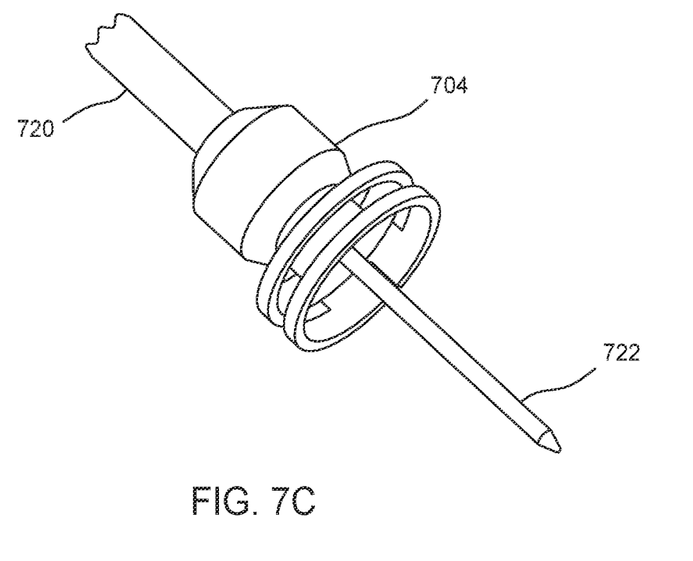

FIGS. 7A-7B depict a cannula assembly 702 and an external retention member 704, which are detachably coupleable to one another. FIG. 7C illustrates the external retention member 704 fixedly coupled to a chandelier illumination probe 720 such that a distal portion of the exposed optical fiber 722 extends therethrough and beyond the external retention member 704.

Cannula assembly 702 is used in conjunction with a trocar, which is used to create an incision in the eye to guide cannula assembly 702 therethrough, as one of ordinary skill in the art appreciates. Cannula assembly 702 mas then remain in the eye throughout the ophthalmic procedure to protect the incision sidewall from repeated contact by surgical instruments that are inserted into the eye through cannula assembly 702.

In certain embodiments, the cannula assembly 702 includes a cannula 706 and a cannula hub 708. The cannula 706 has openings 710, 712 at either end, which are connected by a hollow passageway. In certain embodiments, a valve covers the cannula hub 708. For example, a cannula hub 708 may include a valve at a central portion thereof, which is aligned with the openings of the cannula 706, and through which the trocar, which is used to insert the cannulated entry system 700 through the eye, may be withdrawn. In certain other embodiments, cannula hub 708 is not valved.

In certain embodiments, the external retention member 704 includes a proximal barreled portion 716 and a distal coupling portion 718. As set forth above, the proximal barreled portion 716 and the distal coupling portion 718 have a passageway through which the distal portion of the exposed optical fiber 722 (shown in FIG. 7C) of the chandelier illumination probe 720 is disposed during the manufacturing method. The exposed optical fiber 722 is then fixedly coupled to the external retention member 704 such that a certain portion of the exposed optical fiber 722 extends beyond the external retention member 704.

In operation, the surgeon at least partly inserts the distal coupling portion 718 of the chandelier illumination probe 720 into the cannula assembly 702 and then attaches the external retention member 704 to the cannula hub 708. Attaching the chandelier illumination probe to the cannula assembly 702 in this manner, in certain embodiments, ensures that the chandelier illumination probe 720 remains in place and is not pulled out inadvertently, for example as a result of a minimal pull force.

As shown in FIG. 7B, the external retention member 704 is detachably coupled to the cannula assemble 702, for example, using a snap fit mechanism by which the distal coupling portion 718 slides over and couples to the cannula hub 708. More particularly, the distal coupling portion 718 of the external retention member 704 couples to the external side of the cannula hub 708. For example, in certain embodiments, a circular rim 714 of cannula hub 708 has an outer diameter that is slightly larger than an inner diameter of an opening of the distal coupling portion 718. As shown, the distal coupling portion 718 comprises a slit 724 that allow s the circular opening or inner diameter of the distal coupling portion 718 to enlarge or expand. Therefore, as the distal coupling portion 718 is pushed against the circular rim 714, the opening of the distal coupling portion 718 expands and receives the circular rim 714, thereby allowing the distal coupling portion 718 to slide over and couple to the cannula hub 708. In certain embodiments, although attaching the distal coupling portion 718 and cannula hub 708 protects against the chandelier illumination probe being inadvertently pulled out, the distal coupling portion 718 and the cannula hub 708 are configured to detach in response to a large amount of pulling force applied to the chandelier illumination probe. In such embodiments, when too much pulling force is applied to the chandelier illumination probe, the opening of the distal coupling portion 718 expands again and releases the circular rim 114.

Figure 7D:
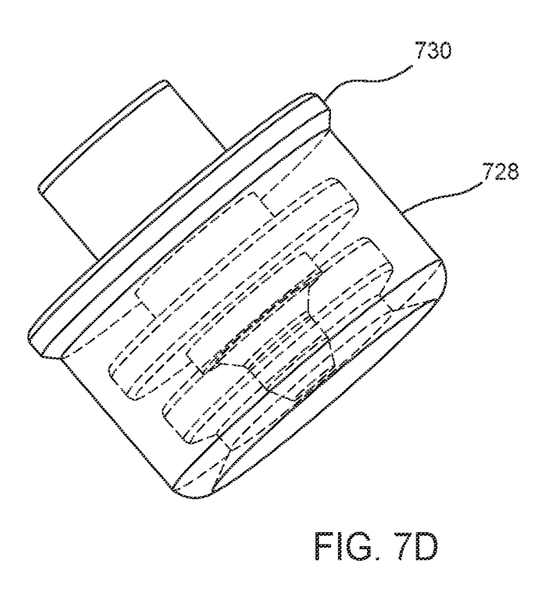

In certain alternative embodiments, the distal coupling portion of an external retention member, such as external retention member 704, includes an overmolded elastomeric piece 728 that slips oxer a cannula hub 730, as shown in FIG. 7D. Like the distal coupling portion 718, the overmolded elastomeric piece 728 provides a mechanism for detachably coupling the external retention member 704 to a cannula, such as cannula 706. The overmolded elastomeric piece 728 is flexible rather than rigid.

Figure 8A:
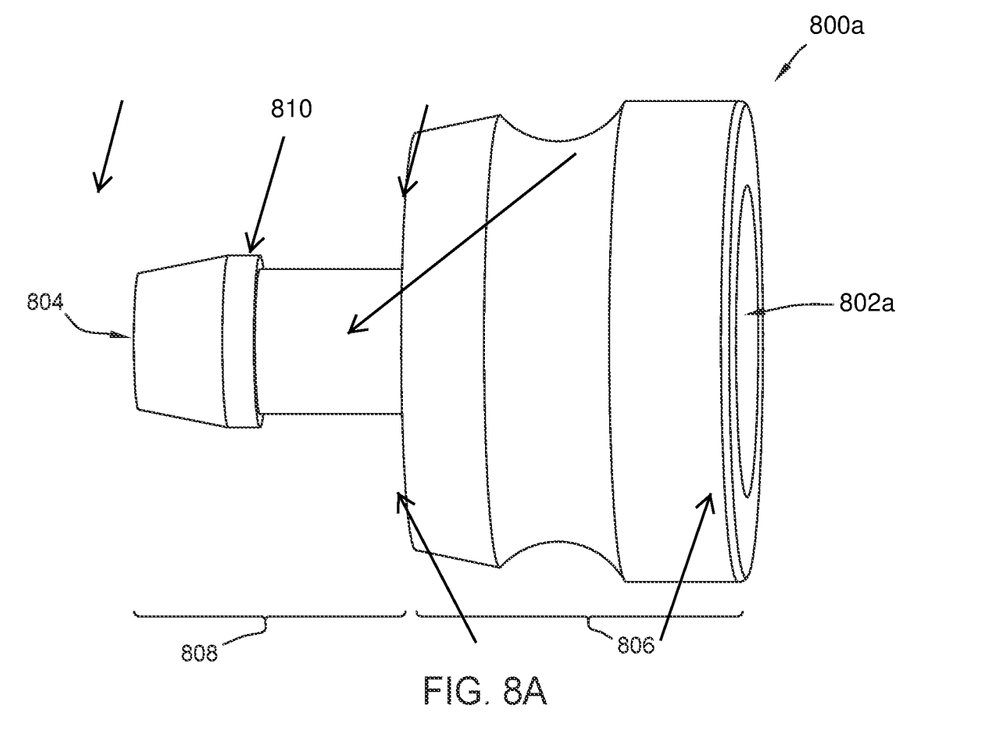
FIGS. 8A-8D illustrate internal retention member(s), in accordance with certain embodiments of the present disclosure.
Figure 8B:
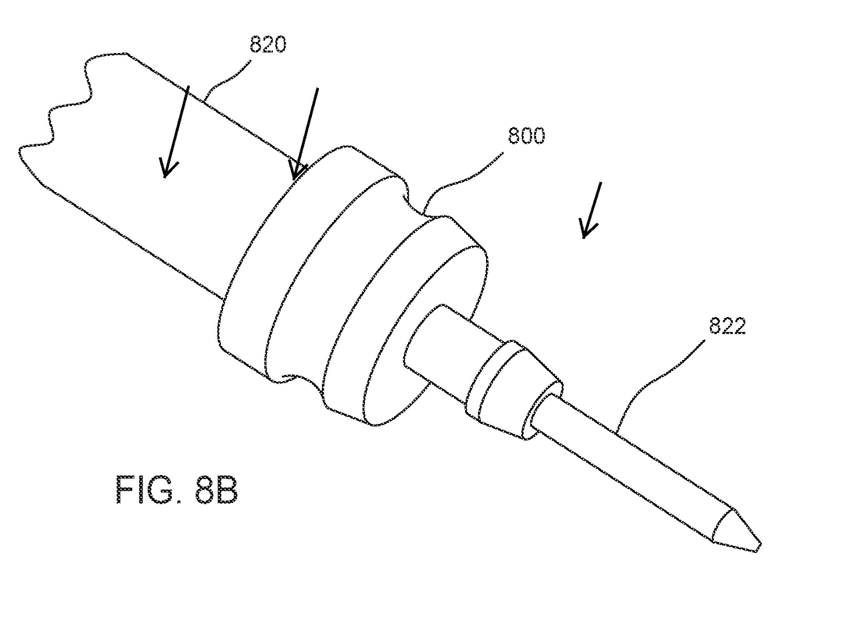

FIG. 8A illustrates an internal retention member 800a. FIG. 8B illustrates the internal retention member 800a fixedly coupled to a chandelier illumination probe 820 such that a distal portion of the exposed optical fiber 822 extends therethrough and beyond the internal retention member 800a. In certain embodiments, the internal retention member 800a includes a passageway that extends from the proximal end 802 to the distal end 804, which aligns with cannula 706 and the cannula huh 708 of the cannula assembly 702, and through which the exposed optical fiber 822 extends, as shown in FIG. 8B. The outer diameter of the proximal portion 806 is greater than the diameter of the distal portion 808. Like the external retention member 704, the internal retention member 800a having a proximal end 802 and a distal end 804 is detachable coupleable to a cannula assembly, such as the cannula assembly 702.

More particularly, when the distal end 804 of the internal retention member 800a is inserted into an opening of the cannula hub 708, a detent 810a of the distal end 804 couples to the cannula huh 708. As shown, the cannula hub 708 includes a salved opening 726 into which the distal end 804 of the internal retention member 800a is inserted. When the distal end 804 is fully pushed past the valve and into the opening 726, the detent 810a of the distal end 804 is then used to retain the distal end 804 in the cannula hub 708. More specifically, in response to a slight and or inadvertent pull force, the valve pushes against the detent 810a, thereby ensuring that the distal end 804 is not pulled out. In certain embodiments, although attaching the internal retention member 800a and the cannula hub 708 protects against the chandelier illumination probe being inadvertently pulled out, the internal retention member 800a and the cannula hub 708 are configured to detach in response to a large amount of pulling force applied to the chandelier illumination probe.

In such embodiments, when too much pulling force is applied to the chandelier illumination probe, the valve opens up and releases the detent 810a.

Figure 8C:
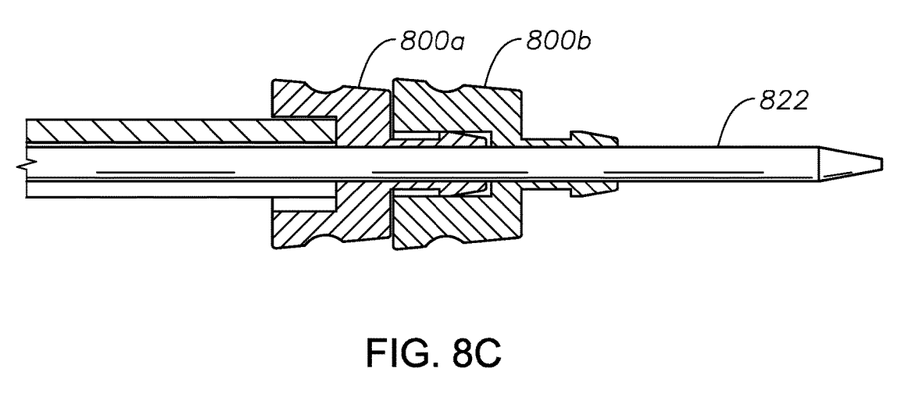
Figure 8D:
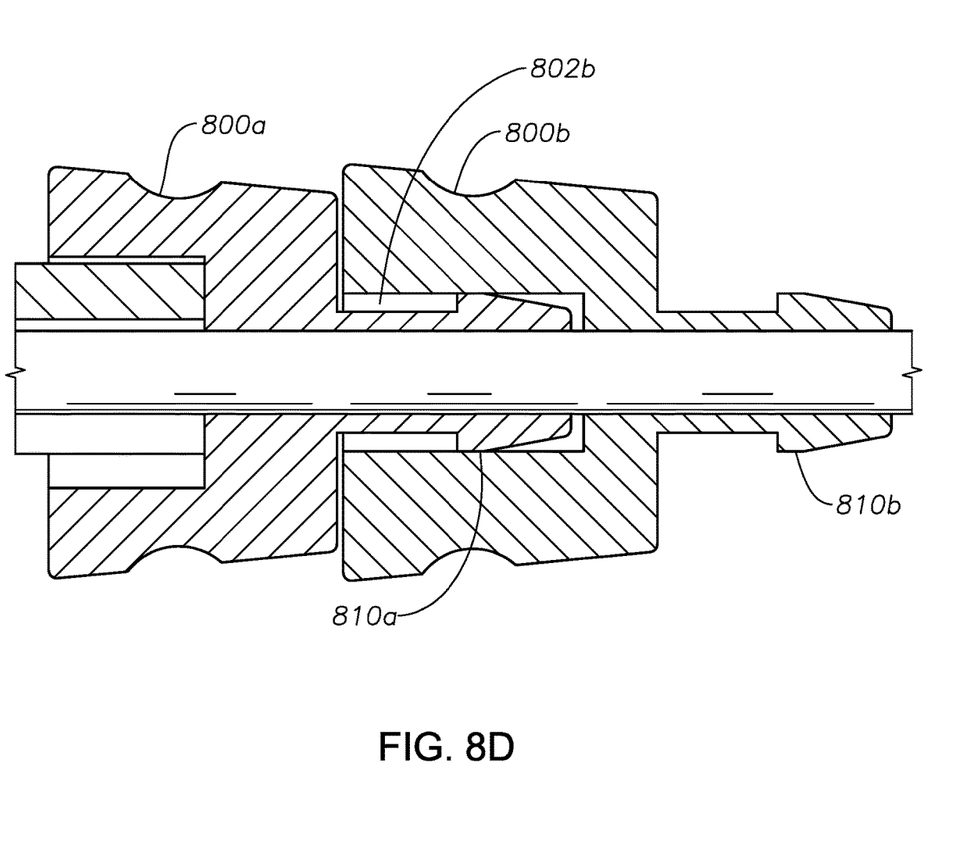

In some embodiments, as seen in FIGS. 8C-D, additional internal retention member(s) 800b can be used to change the depth the exposed optical fiber 822 extends below the distal end 804 (of the last internal retention member 800b added to the internal retention member 800a). The change in depth will translate to a change in depth of a length of the fiber extending through the cannula assembly and into the eye (allowing the surgeon to move the optical fiber tip to a desired depth in the eye). As seen in FIGS. 8C-D, one additional internal retention member 800b is used by engaging the detent 810a of the upper internal retention member 800a with the opening 802b of the lower internal retention member 800b. Additional internal retention members can be added by engaging the detents 810 and openings 802 sequentially as internal retention members are added. The detent 810a may engage opening 802b through a friction fit that can be overcome by pulling apart internal retention member 800a and internal retention member 800b. Other detent/retention formations are also possible. For example, small detents (not shown) may stick out of the top portion of 800b to engage into receiving recesses (also not shown) on the bottom surface of 800a. These detents/recesses may also engage through a friction fit.

In addition to the improved, formable chandelier illumination systems, which are flexible and low profile, set forth herein, the present disclosure also contemplates methods for belling and combining optical fibers to improve light coupling efficiency and reduce fiber position sensitivity, and provide dual chandelier systems using a single connector. According to embodiments of the present disclosure, belling of one or more optical fibers, such as a plurality of optical fibers, is accomplished by heating the end(s) of the one or more optical fibers until the end "bells" or flares to an expanded diameter. More particularly, when heated, a plastic optical fiber shortens and swells, thus increasing the diameter of each of the one or more optical fibers. After the one or more optical fibers have been belled, the belled proximal end(s) are then be pulled back through an opening, such as the opening at the proximal end of a connector (e.g., connector 106) for connection to a surgical console, while the one or more optical fibers are formable from the heating method. Once the belled optical fibers have been pulled back into the opening, the diameter of the one or more belled portions of the optical fibers becomes the same as, or smaller than, the diameter of the opening into which the one or more belled optical fibers are withdrawn, but larger than the unbelted portion of the optical fiber.

The increased diameter after belling is about 1.5 or 2 times greater than the original diameter of the optical fiber. According to embodiments of the present disclosure, it is the proximal end of the optical fiber that is heated. In operation, the increased diameter of the proximal end of the one or more optical fibers corresponds to an increased light coupling efficiency from the light source and reduces the fiber position sensitivity. In some embodiments, the increased diameter of the belled optical fiber can be made to match the width of the beam provided by the light source through the connector to increase the photopic throughput of the belled optical fiber over conventional chandelier illumination systems.

It is contemplated that the disclosed malleable and preformed optical fibers disclosed herein may be belled and combined according to certain embodiments of the present disclosure.

Figure 9A:
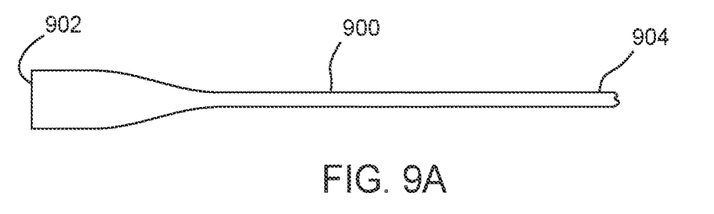
FIGS. 9A-9B illustrate a cross-sectional view and a side view, respectively, of a single optical fiber that is belled, in accordance with certain embodiments of the present disclosure.
Figure 9B:
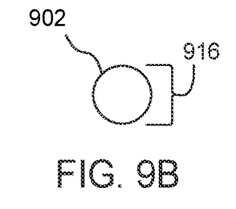
Figure 12:
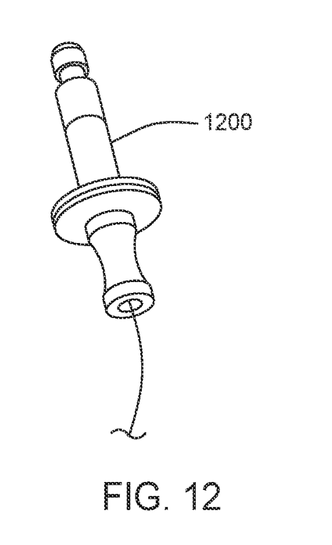
FIG. 12 illustrates a single chandelier connector for connecting with a surgical console, in accordance with certain embodiments of the present disclosure.

FIGS. 9A-9B illustrate a cross-sectional view and a side view, respectively, of a single optical fiber 900 that is belled. As shown in FIG. 9A, the proximal end 902 of the optical fiber 900 is belled according to methods disclosed herein such that the diameter of the proximal end 902 is greater than the diameter of the distal end 904. Thus, the light coupling efficiency of the belled proximal end 902 is increased and the fiber position sensitivity is reduced. After being drawn into an opening of desired diameter, such as the opening 916 at the proximal end of a single chandelier connector 1200 (i.e., a connector configured for coupling the optical fiber of one chandelier illumination probe to a surgical console) shown in FIG. 12, the belled proximal end 902 has the same size, shape, and diameter as that of the opening 916 through which it was drawn, as shown in FIG. 9B. In certain embodiments, the single chandelier connector 1200 is used to connect the belled single optical fiber 900 with a surgical console, such as the surgical console 104 shown in FIG. 1.

Figure 10A:
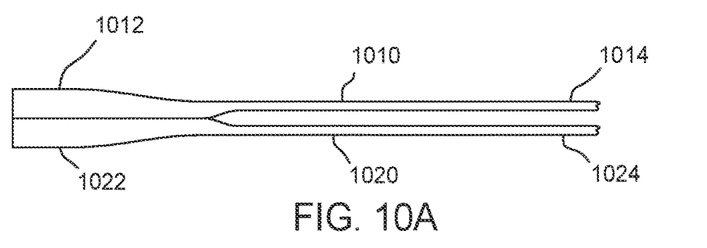
FIGS. 10A-10B illustrate a cross-sectional view and a side view, respectively, of two optical fibers that have been belled and combined, in accordance with certain embodiments of the present disclosure.
Figure 10B:
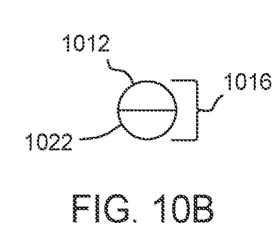
Figure 13:
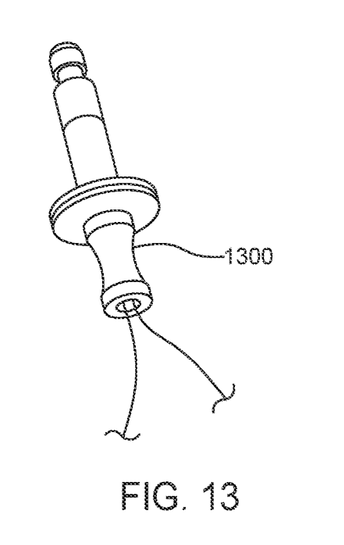
FIG. 13 illustrates a dual chandelier connector for connecting with a surgical console, in accordance with certain embodiments of the present disclosure.

FIGS. 10A-10B illustrate a cross-sectional view and a side view, respectively, of two optical fibers 1010 and 1020 that have been belled and combined. As shown in FIG. 10A, the proximal ends 1012, 1022 of the optical fibers 1010, 1020 have been belled according to methods disclosed herein such that the diameter of the circular proximal end of the combined proximal ends 1012, 1022 is greater than the diameter of the distal portions 1014, 1024. Thus, the light coupling efficiency of the belled proximal ends 1012, 1022 is increased. As shown in FIG. 10B, after being drawn into an opening of desired diameter, such as the proximal opening 1016 of a dual chandelier connector 1300 (i.e., a connector configured for coupling the optical fibers of two chandelier illumination probes to a surgical console) shown in FIG. 13 for connecting with a surgical console, such as console 104 shown in FIG. 1, the belled proximal ends 1012, 1022, are combined and have the same size, shape, and diameter as that of the opening 1016 through which they were drawn. Note that, in certain embodiments, the single chandelier connector 1200 may also be used in coupling optical fibers 1010 and 1020 to a surgical console as well. In the example shown in FIG. 10B, each of the proximal ends 1012, 1022 has a D-shaped cross-section, which in combination fill the opening and take the same shape, size, and diameter of the opening 1016 of the dual chandelier connector. In operation, the distal portions 1014, 1024 remain uncombined such that the two, separate optical fibers 1010 and 1020 create a dual chandelier system that can be used to illuminate areas, such as a surgical site in patient's inner eye, while using a single chandelier connector.

Figure 11A:
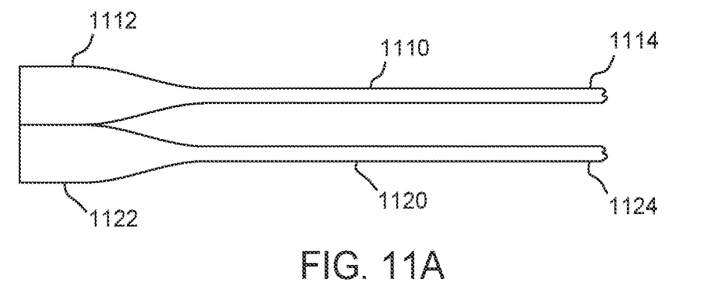
FIGS. 11A-11B illustrate a cross-sectional view and a side view, respectively, of two optical fibers that have been belted and combined, in accordance with certain embodiments of the present disclosure.
Figure 11B:
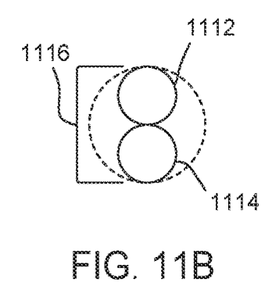

FIGS. 11A-11B illustrate a cross-sectional view and a side view, respectively, of two optical fibers 1110 and 1120 that have been belled and combined. As shown in FIG. 11A, the proximal ends 1112, 1122 of the optical fibers 1110, 1120 have been belled according to methods disclosed herein such that the diameters of the proximal ends 1112, 1122 are greater than the diameter of the distal portions 1114, 1124, respectively. Thus, the light coupling efficiency of the belled proximal ends 1112, 1122 is increased. As shown in FIG. 11B, after being drawn into an opening of desired diameter, (e.g., the opening of a chandelier connector such as chandelier connector 1300 shown in FIG. 13 for connecting with a surgical console, such as console 104 shown in FIG. 1), the belled proximal ends 1112, 1122, are combined side-by-side within the opening through which they were drawn. In the example shown in FIG. 11B, each of the proximal ends 1112, 1122 has an increased diameter and is positioned side-by-side, within the diameter of the opening 1116 of the dual chandelier connector. In operation, the distal portions 1114, 1124 remain uncombined such that the two, separate optical fibers 1110 and 1120 create a dual chandelier system that can be used to illuminate areas, such as a surgical site in patient's inner eye. Note that, in certain embodiments, a dual chandelier connector, such us the dual chandelier connector 130 may have different proximal opening diameters for accommodating the different sizes of the combined belled proximal ends of optical fibers (e.g., optical fibers 1012/1022 or optical fibers 1112/1114).

Figure 14A:
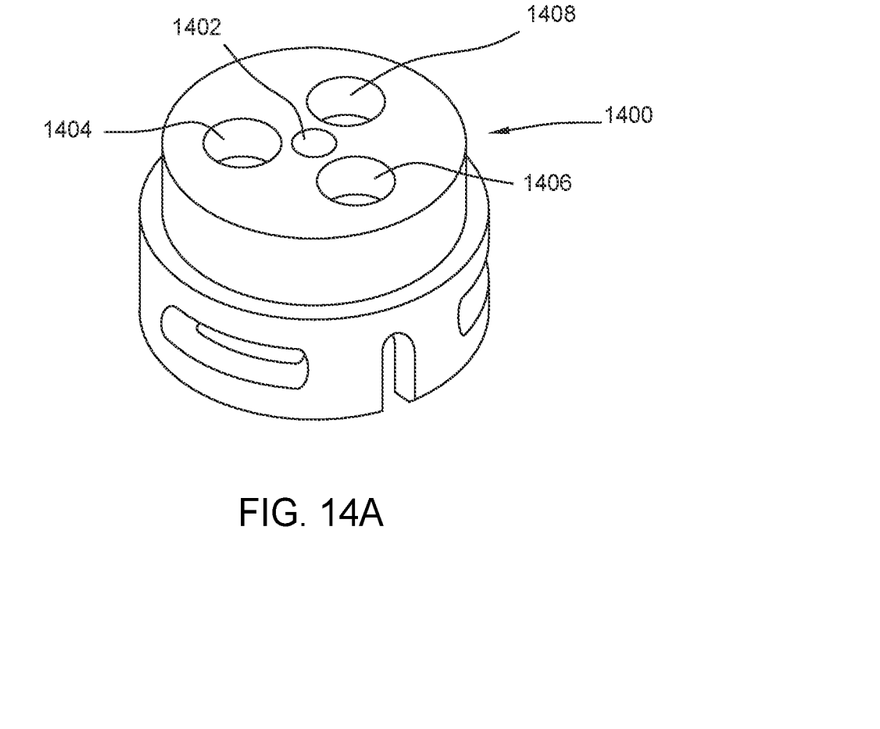
FIGS. 14A-14B illustrates a moveable stopper, in accordance with certain embodiments of the present disclosure.
Figure 14B:
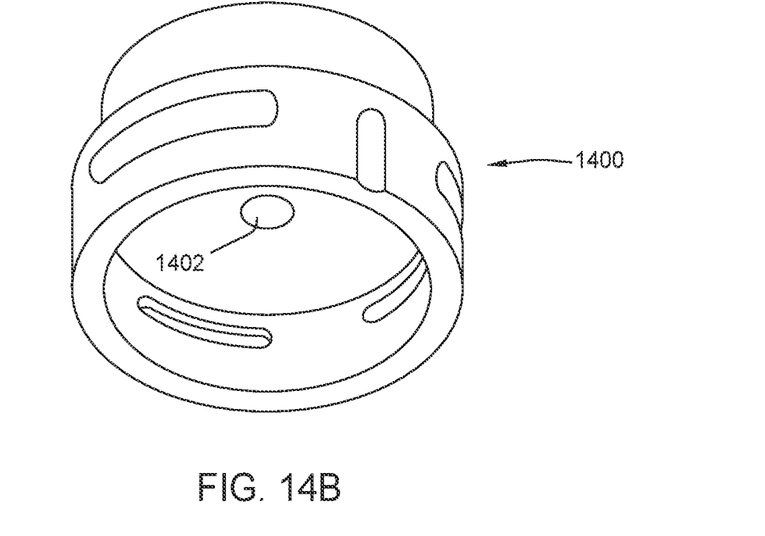

FIGS. 14A-14B illustrate a moveable shipper 1400, in accordance with certain other embodiments of the present disclosure. The moveable stopper 1400, which may be used in place of moveable stoppers 312 and 512, is configured to press on an optical fiber along which it is disposed and allow for tolerance room based on tolerance inherent to the optical fiber. The moveable shipper 1400 comprises a flexible material. In operation, when the optical fiber is pushed through the moveable stopper 1400, such as through the centrally-disposed opening 1402, the walls of the three compliant members (e.g., pillars 1404, 1406, and 1408) flex and impede on the internal diameter of the centrally-disposed opening 1402. The complaint members catch on to the external diameter of the optical fiber disposed therethrough to provide a stopper mechanism for preventing the optical fiber from being advanced too far into the patient s eye. More particularly, the flexing of the compliant members increases the friction between the moveable stopper 1400 and the optical fiber disposed therethrough to prevent the user from over advancing the optical fiber into the patient's eye. Likewise, the flexing of the compliant members provides increased retention of the optical fiber during the procedure. In certain embodiments, moveable stoppers 312 and 512 may be configured with similar compliant members.

Figure 15A:
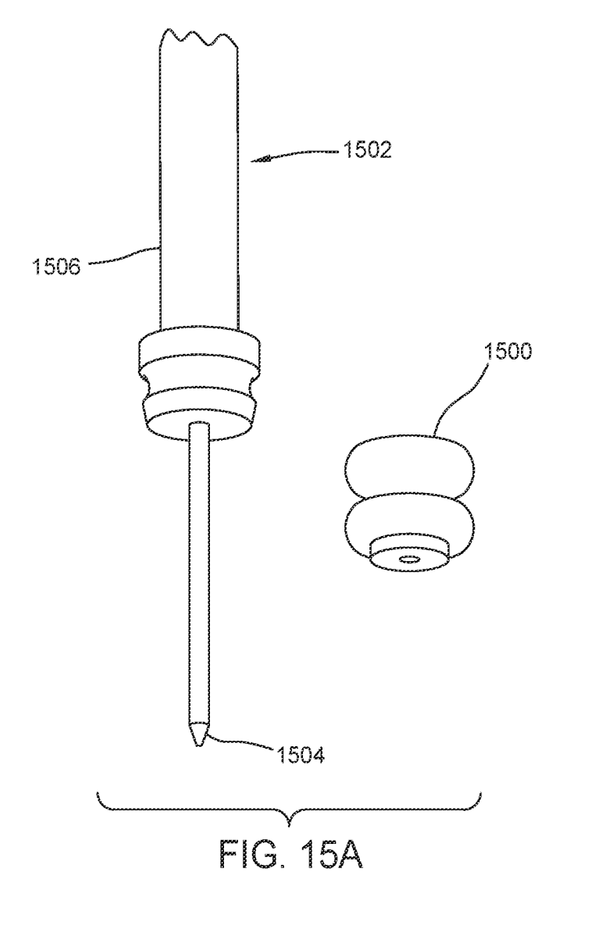
FIGS. 15A-15B illustrate a removable spacer, in accordance with certain embodiments of the present disclosure.
Figure 15B:
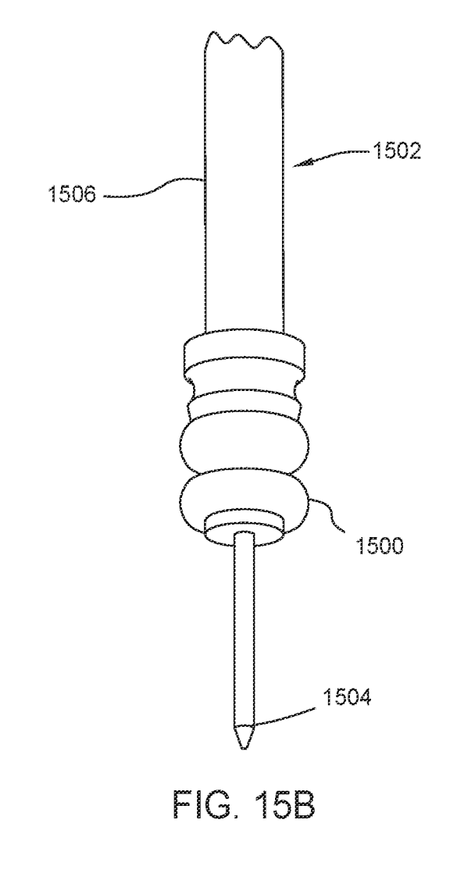

FIGS. 15A-15B illustrate a removable spacer 1500 and a chandelier illumination probe 1502, in accordance with certain embodiments of the present disclosure. As shown in FIG. 15A, the spacer 1500 is disposed along a chandelier illumination probe 1502, such that a proximal end of the spacer is in contact with the distal end of the sleeve 1506. As shown, the distal portion of the exposed optical fiber 1504 extends therethrough and beyond the spacer 1500. In operation, the desired insertion depth range of an optical fiber during ophthalmic procedures is between about 2.5 mm and about 6 mm, depending on the length of the cannula. The spacer 1500 is removable such that if an insertion depth of between 2 mm and 4 mm is desired, for example, the spacer 1500 would be about 2 mm. In that example, when the spacer 1500 is disposed on the exposed optical fiber 1504, what remains exposed for insertion is 2 mm of optical fiber 1504 suitable for the desired 2 mm insertion depth into a patient's eye, as shown in FIG. 15A. If a 4 mm insertion is desired, the removable spacer 1500 is removed (for example, through a slit in the side of the spacer 1500) such that 4 mm of exposed optical fiber 1504 remains exposed for insertion into the patient's eye, as shown in FIG. 15B. The length of the removable spacer 1500 is between about 2 mm and about 4 mm.

In certain embodiments, the disclosed ergonomic chandelier illumination systems are low in weight, flexible to form any desired shape, and low profile to prevent interference with an optical microscope or other equipment positioned above or otherwise around the patient's eye during ophthalmic surgery. In addition, the disclosed ergonomic chandelier illumination systems are suitable for cannulated and or non-cannulated insertion into the patient's eye.

In addition, in certain embodiments, the disclosed method advantageously bells and binds two optical fibers together at the proximal end such that there are two individual chandeliers at the distal end with a single connector at the proximal end.

Accordingly, devices, systems, and methods are provided for providing improved illumination of an area internal to the eye, for example a surgical site during ophthalmic surgery since the disclosed chandelier illumination systems have improved flexibility, profile, and light coupling efficiency.

EXAMPLE EMBODIMENTS

Embodiment 1: A chandelier illumination probe, comprising: a metal wire; an optical fiber; and a sleeve. The metal wire and the optical fiber are housed within the sleeve. The metal wire, the optical fiber, and the sleeve are bound at a binding. An exposed distal portion of the optical fiber extends beyond a distal end of the sleeve. The metal wire comprises a malleable material configured for being bent to an angle before or during a surgical procedure.

Embodiment 2: The chandelier illumination probe of Embodiment 1, wherein: the chandelier illumination probe is fixedly coupled to an external retention member, the external retention member is configured to be detachably coupled to a cannula assembly, and when the external retention member is coupled m the cannula assembly, the external retention memory retains the chandelier illumination probe within the cannula assembly when at least an amount of pulling force is applied to the chandelier illumination probe.

Embodiment 3: The chandelier illumination probe of Embodiment 2, wherein a circular rim of the cannula hub is disposed in a slit of the distal coupling portion such that a snap fit coupling is provided between the distal coupling portion of the external retention member and the cannula hub.

Embodiment 4: The chandelier illumination probe of Embodiment 1, wherein: the chandelier illumination probe is fixedly coupled to an internal retention member, the internal retention member is configured to be detachably coupled to a cannula assembly, and when the internal retention member is coupled to the cannula assembly, the internal retention memory retains the chandelier illumination probe within the cannula assembly when at least an amount of pulling force is applied to the chandelier illumination probe.

Embodiment 5: The chandelier illumination probe of Embodiment 4, wherein when a distal end of the internal retention member is inserted into an opening of the cannula hub, a decent of the distal end couples to the cannula hub.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A chandelier illumination probe, comprising:
 a metal wire;
 an optical fiber; and
 a sleeve, wherein:
  the metal wire and the optical fiber are housed within the sleeve;

the metal wire, the optical fiber, and the sleeve are bound together at a binding with an adhesive;

the metal wire terminates at the binding;

an exposed distal portion of the optical fiber extends beyond a distal end of the sleeve; and the metal wire comprises a malleable material configured for being bent to an angle before or during a surgical procedure.

2. The chandelier illumination probe of claim 1, wherein a diameter of the metal wire is between about 0.1 millimeter and about 0.5 millimeters; and wherein a diameter of the sleeve is between about 0.5 millimeters and 1.5 millimeters.

3. The chandelier illumination probe of claim 1, further comprising a moveable stopper disposed between the binding and a distal end of the exposed distal portion of the optical fiber, the moveable stopper comprising one or more compliant members disposed therein and configured for increasing friction between the moveable stopper and the optical fiber.

4. The chandelier illumination probe of claim 1, further comprising:

a retention member, wherein the chandelier illumination probe is fixedly coupled to the retention member;

wherein the retention member is configured to be detachably coupled to a cannula assembly; and when the retention member is coupled to the cannula assembly, the retention member retains the chandelier illumination probe within the cannula assembly when at least an amount of pulling force is applied to the chandelier illumination probe.

5. The chandelier illumination probe of claim 1, further comprising:

a first retention member, wherein the chandelier illumination probe is fixedly coupled to the first retention member;

a second retention member, wherein the second retention member is configured to be detachably coupled to the first retention member and wherein the optical fiber extends through both the first retention member and the second retention member;

wherein the second retention member is configured to be detachably coupled to a cannula assembly; and when the second retention member is coupled to the cannula assembly, the second retention member retains the chandelier illumination probe within the cannula assembly when at least an amount of pulling force is applied to the chandelier illumination probe.

6. The chandelier illumination probe of claim 1, further comprising a removable spacer, a proximal end of the removable spacer being disposed in contact with the distal end of the sleeve, and wherein a length of the removable spacer is between about 2 millimeters and about 4 millimeters.

7. The chandelier illumination probe of claim 1, wherein a proximal end of the optical fiber is belled.

8. The chandelier illumination probe of claim 1, further comprising a guiding needle configured for creating an opening in a patient's eye wall through which the chandelier illumination probe is inserted.

9. The chandelier illumination probe of claim 1, wherein the binding is located at the distal end of the sleeve.

* * * * *